US007842508B2

(12) United States Patent
Palermo et al.

(10) Patent No.: US 7,842,508 B2
(45) Date of Patent: Nov. 30, 2010

(54) METHOD FOR DETERMINING THE GAS HYDRATE ANTI-AGGLOMERATION POWER OF A WATER/OIL SYSTEM

(75) Inventors: Thierry Palermo, La Garenne Colombes (FR); Lionel Rousseau, Issou (FR); Christine Dalmazzone, Versailles (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 1288 days.

(21) Appl. No.: 11/182,837

(22) Filed: Jul. 18, 2005

(65) Prior Publication Data

US 2006/0020151 A1 Jan. 26, 2006

(30) Foreign Application Priority Data

Jul. 20, 2004 (FR) .................... 04 08058

(51) Int. Cl.
*G01N 25/00* (2006.01)
*G01N 37/00* (2006.01)
(52) U.S. Cl. .............. 436/147; 422/68.1; 422/69; 73/19.01; 73/53.01; 73/579
(58) Field of Classification Search .......... 436/147; 422/68.1, 69; 73/19.01, 53.01, 579
See application file for complete search history.

(56) References Cited

U.S. PATENT DOCUMENTS 6,015,929 A * 1/2000 Rabeony et al. ............. 585/15

6,298,724 B1 10/2001 Burgass et al.
2002/0107256 A1 * 8/2002 Thiele et al. ............. 514/262.1
2002/0134136 A1 * 9/2002 Dalmazzone et al. ...... 73/25.01

FOREIGN PATENT DOCUMENTS

FR 2820823 9/2002

OTHER PUBLICATIONS

Dalmazzone C et al: "Prediction of Gas Hydrates Formation with DSC Technique PRC SPE Annu Tech Conf Exhib; Proceedings—SPE Annual Technical Conference and Exhibition" 2003, 2003, pp. 2331-2338, XP008040876.
Koh C A et al: "A Dynamic Study of the Formation of Gas Clathrate Hydrates: In-Situsynchrotron X-Ray Diffraction and Differential Scanning Calorimetry" Materials Science Forum, Aedermannsfdorf, CH, vol. 228-231. 1996, pp. 239-243, XP001051691.
Danesh A: "Hydrate Equilibrium Data of Methyl Cyclopentane with Methane or Nitrogen" Chemical Engineering Research and Design, Part A Institution of Chemical Engineers, XX, vol. 72, Mar. 1994, pp. 197-200, XP002071473.

* cited by examiner

*Primary Examiner*—Krishnan S Menon
*Assistant Examiner*—Rebecca Fritchman
(74) *Attorney, Agent, or Firm*—Millen, White, Zelano & Branigan, P.C.

(57) ABSTRACT

In order to determine the gas hydrate anti-agglomeration power of a system composed of an aqueous phase dispersed in a liquid hydrocarbon phase in the presence of a gas, at least two successive cycles of hydrate formation and dissociation is carried out by cooling and reheating a sample of said system placed in the cell of a calorimeter to record thermograms; the anti-agglomeration power of said system is determined by comparing the thermograms obtained during the various cycles.

9 Claims, 3 Drawing Sheets

METHOD FOR DETERMINING THE GAS HYDRATE ANTI-AGGLOMERATION POWER OF A WATER/OIL SYSTEM

BACKGROUND OF THE INVENTION

1. Field of the Invention

The present invention relates to the problem of plugging transport lines with gas hydrates during the oil and/or gas production. It may also be applied to other fields such as those of drilling mud or of transporting gas in the form of hydrates.

It concerns a method for determining the gas hydrate anti-agglomeration power of a system composed of an aqueous phase dispersed in a liquid hydrocarbon phase in the presence of a gas.

Gas hydrates are crystalline compounds which may form under pressure and at low temperatures when water is in contact with gas molecules. Such conditions are generally encountered during the production of oil and/or gas, in particular under deepwater conditions. Formation of such hydrates can lead to the formation of a plug by an agglomeration mechanism. In the case of the presence of a liquid hydrocarbon phase (production of oil or condensate gas), water may be in the form of droplets dispersed in the liquid hydrocarbon phase. We then have a water-in-oil emulsion the stability of which is linked to the presence of natural surfactants or additives.

The invention proposes a method for determining the agglomeration of hydrates for systems essentially consisting of emulsified water-in-oil systems. This method, as was described above, is of interest to the production of oil and condensate gas, but also to drilling operations using oil-based mud constituted by an aqueous phase dispersed in an oily phase.

2. Description of Related Art

Operational solutions currently employed to prevent the formation of hydrate plugs in lines essentially consist of using thermally insulated lines or injecting thermodynamic inhibitors. In both cases, the production conditions are kept outside the hydrate stability zone. This stability zone, in terms of pressure and temperature, is determined from tests carried out in a PVT cell or by using thermodynamic models. More recently, a method using a high pressure calorimeter has been proposed (French patent FR-B-2 820 823) in the case of drilling mud.

More rarely, it has been envisaged to inject:
- kinetic inhibitor additives (Corrigan A, Duncum S N, Edwards A R and Osborne C G, SPE 30696 presented at the SPE Annual Technical Conference and Exhibition, Dallas, Oct. 22-25, 1995);
- or anti-agglomeration additives (AA) (Mehta A P, Herbert P B, Cadena E R and Weatherman J P, "Fulfilling the promise of low dosage hydrate inhibitors: Journey from academic curiosity to successful field implementation", OTC 14057, Houston, Tex., 6-9 May 2002).

Finally, problems linked to the formation of hydrate plugs can be expected to be avoided because of the presence of natural surfactants in the oil (Palermo T, Mussumeci A, Leporcher E: "Could hydrate plugging be avoided because of surfactant properties of the crude and appropriate flow conditions?" OTC 16681, Houston, Tex., 3-6 May 2004). AA (anti-agglomeration) additives and natural surfactants cannot prevent the formation of hydrate particles, but prevent the latter from agglomerating. Hydrate particles may thus be transported in the form of a suspension without the formation of a plug.

However, generalizing the concept of hydrate transport in the form of a suspension suffers from a lack of a simple, reliable evaluation means. The most highly developed means consist of tests carried out in flow loops approaching real conditions (Palermo T, Maurel P: "Investigation of hydrates formation and hydrates transportation with and without dispersant additives under multiphase flow conditions", in Multiphase '99, $9^{th}$ International Conference on Multiphase, 567-582). However, the difference in scale and the mode of circulation in a loop renders predictions of the risks of plugging under real conditions difficult. Such facilities also require very large quantities of fluid and are thus expensive to use.

BRIEF SUMMARY OF THE INVENTION

The present invention concerns a method for determining the gas hydrate anti-agglomeration power of a system comprising an aqueous phase dispersed in a liquid hydrocarbon phase in the presence of a gas (dissolved or free).

In the description which follows, said system comprising an aqueous phase dispersed in a liquid hydrocarbon phase could be designated both by the expressions "emulsified water-in-oil system" and "water-in-oil emulsion".

The method of the invention is generally characterized in that at least two successive cycles for hydrate formation and dissociation is carried out by cooling and reheating a sample of said system placed in the cell of a calorimeter to produce thermograms; the anti-agglomeration power of said system is determined by comparing the thermograms obtained during different cycles.

More particularly, the anti-agglomeration power of such a system is determined from thermograms obtained using a DSC (differential scanning calorimetry) technique carried out in the usual manner using an apparatus provided with two pressure cells, a measurement cell and a reference cell.

DSC is a technique which allows the heat exchanged between a sample and a reference to be measured as a function of temperature or time. The resultant of such measurements is presented in a form commonly known as a thermogram.

The formation and dissociation of gas hydrates are phenomena which are respectively exothermic and endothermic. They are thus accompanied by an exchange of heat between the sample and the reference which follows the basic equation given below:

$$dh/dt = dq/dt + (C_e - C_r)dT/dt + RC_e d^2q/dt^2$$

in which:
- $dh/dt$ = the heat flow between the sample and reference (W);
- $dq/dt$ = Q = caloric power recorded by the calorimeter (W);
- $C_e$ = heat capacity of the sample (J/K);
- $C_r$ = heat capacity of the reference (J/K);
- T = temperature of thermostatted cell (K);
- t = time (s);
- R = thermal resistance (K/W).

C. In this case, the power (per unit mass of sample) recorded by the calorimeter is expressed as a function of time: Q(t).

Figure 3:
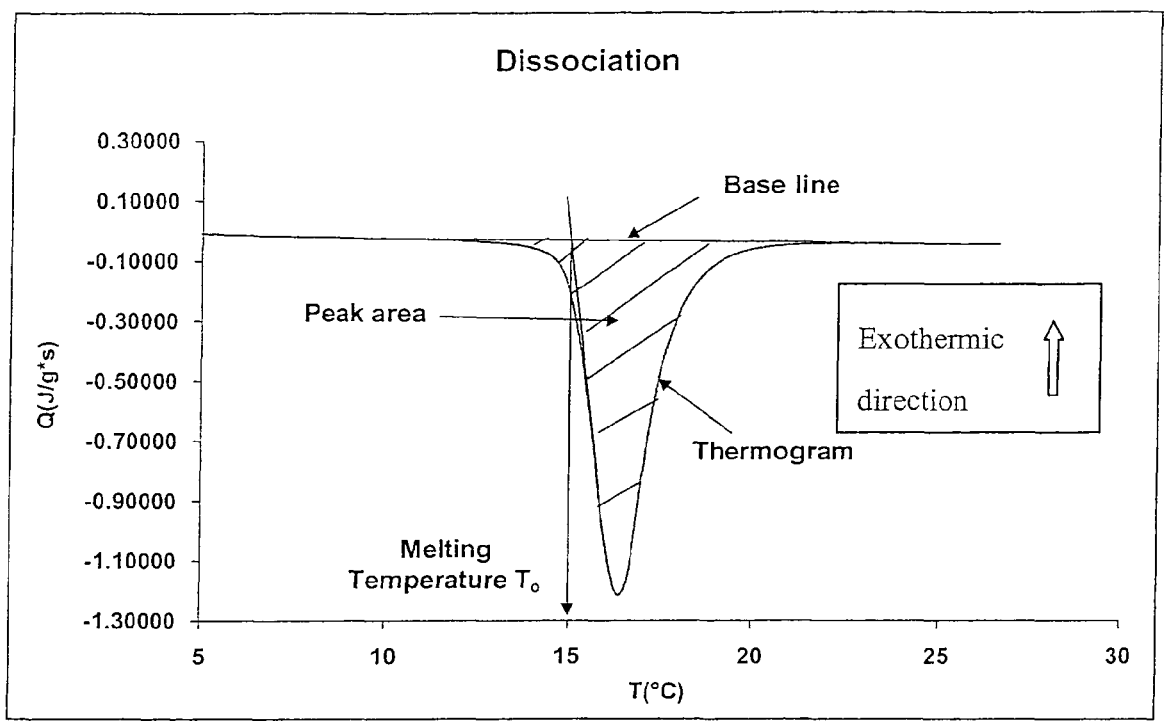

FIG. 3 shows a thermogram corresponding to the formation of hydrates when the temperature is rising. In this case, the power (per unit mass of sample) recorded by the calorimeter is expressed as a function of temperature: Q(T).

Figure 4:
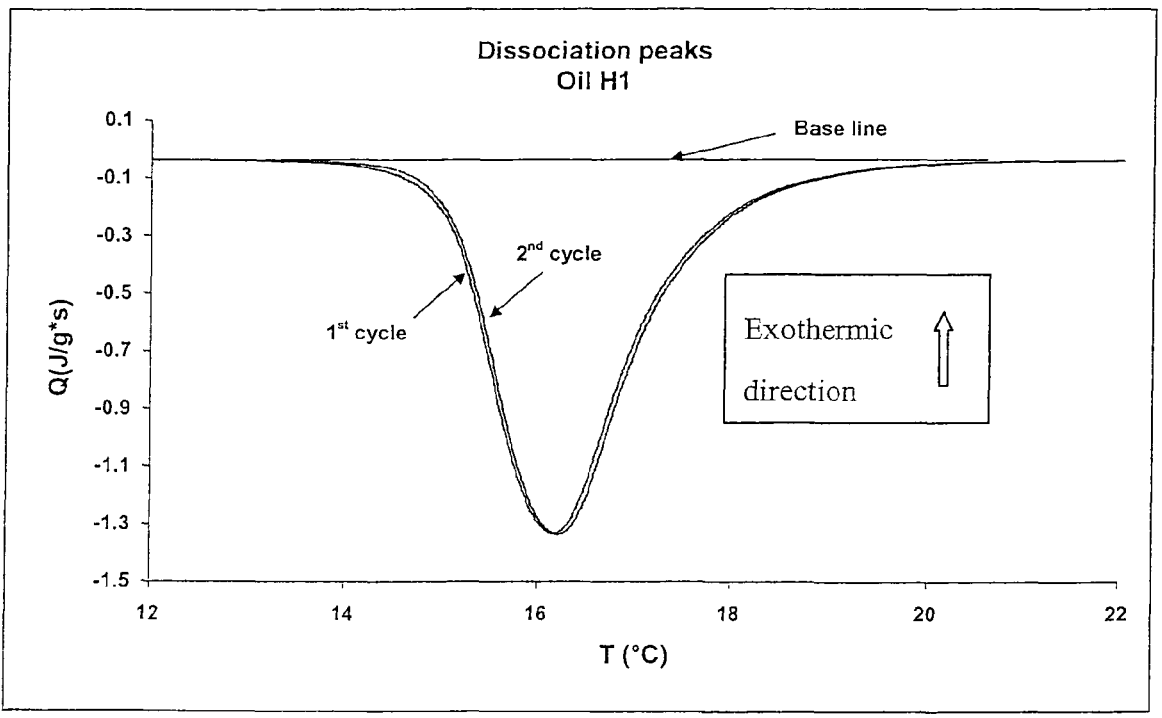
Figure 5:
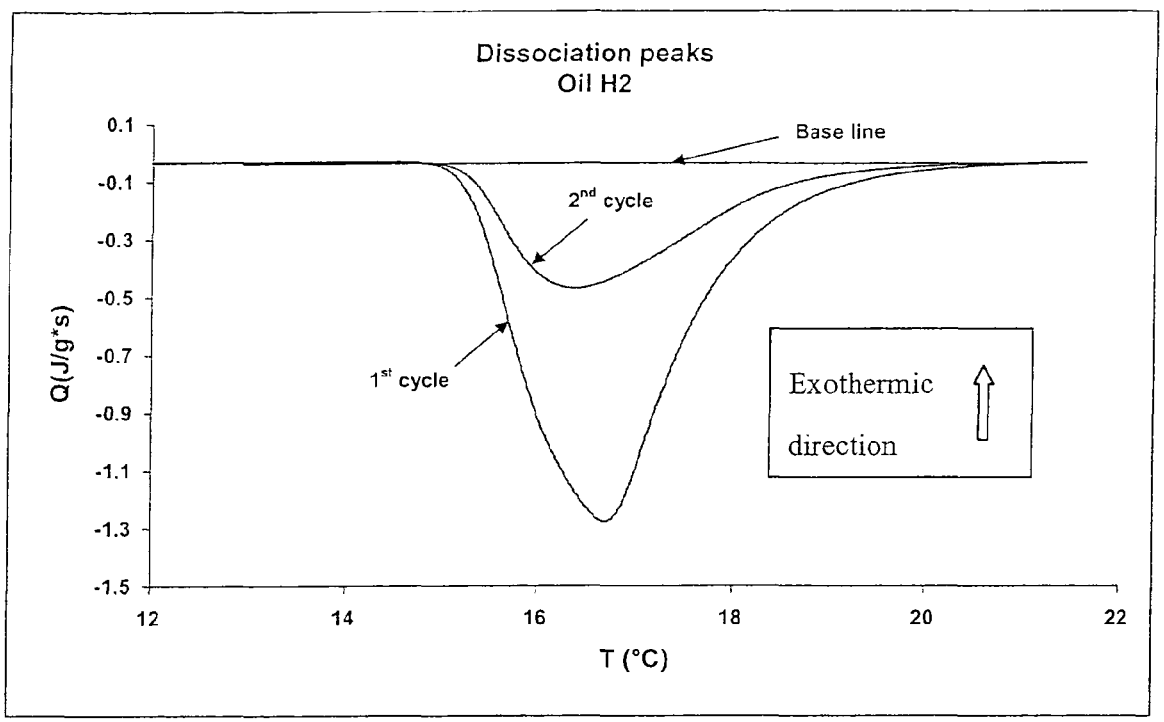
Figure 6:
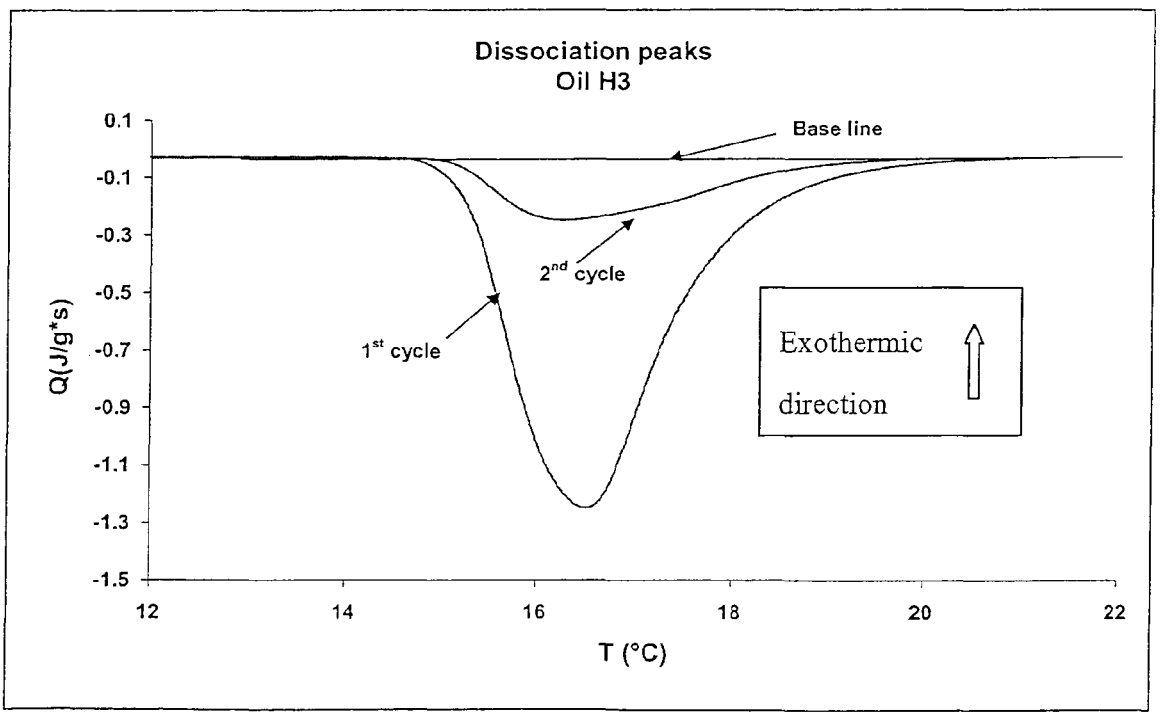

FIGS. 4, 5 and 6 are thermograms recorded during the dissociation phase of two successive cycles discussed below in the Examples.

The area under the peaks, taken between the curve Q(T) or Q(t) and the base line, is directly proportional to the total quantity of hydrates formed. For practical reasons, we recommend the use of dissociation thermograms to determine the quantity of hydrates.

DETAILED DESCRIPTION OF THE INVENTION

More particularly, the method of the invention is characterized in that it comprises the following steps:
a) providing (or preparing) said system, in particular a water-in-oil emulsion;
b) placing a sample of said water-in-oil emulsion in the measuring cell of a calorimeter comprising a measuring cell and a reference cell;
c) placing an equal quantity by weight of an inert body in the reference cell of said calorimeter;
d) bringing the sample and the inert body to a gas pressure P;
e) starting from a temperature $T_1$ which is higher than the melting point $T_0$ of the hydrate, reducing the temperature in the measuring and reference cells to a set temperature $T_2$ which is maintained for a time sufficient to form at least the major portion of the hydrates capable of being formed from the sample located in the measuring cell; preferably, cooling the measuring and reference cells at a temperature ramp-down of 0.5° C. to 5° C. per minute;
f) reheating the measuring and reference cells to a temperature $T_3$ which is higher than the melting point $T_0$ of the hydrate to dissociate the hydrates formed in step (e); preferably, reheating the measuring and reference cells at a temperature ramp-up of 0.5° C. to 5° C. per minute;
g) recording a thermogram on which a peak is identified the area of which, or any other dimension linked to the area, is characteristic of the quantity of hydrates formed;
h) repeating the cycle of steps (e) to (g) at least once;
i) during dissociation of the hydrates in the successive cycle or cycles, identifying in the thermograms a peak the area of which or any other dimension linked to the area is characteristic of the quantity of hydrates formed;
j) from the change in areas (or other dimensions linked to the area) of the successive peaks, determining the gas hydrate anti-agglomeration power of the sample, a reduction in said area (or other dimension) revealing a weak anti-agglomeration power and conservation of said area (or other dimension) revealing a strong anti-agglomeration power.

The gas hydrate anti-agglomeration power of a system composed of an aqueous phase dispersed in a liquid hydrocarbon phase is determined as follows:

The various steps of the method of the invention will now be described in detail.

a) Water-in-Oil Emulsion

A stable water-in-oil emulsion is provided (or prepared). The proportion of water in the emulsion may be 5% to 90% by weight (for 10% to 95% by weight of oil), preferably about 30% by weight of water (for about 70% by weight of oil). The water may be neutral, acidic or basic and may contain dissolved salts. The oil and/or water may contain one or more compounds dissolved as additives having various functions, for example corrosion inhibitors, anti-deposition additives (minerals, paraffins, asphaltenes), anti-foaming additives, emulsifying additives, de-emulsifying additives or anti-hydrate additives (thermodynamic inhibitors, kinetic inhibitors).

When a water-in-oil emulsion is prepared, it recommended that this emulsion be prepared in a manner such that water droplets with a radius of the order of 1 to 10 μm are obtained. Under these conditions, the most probable temperature for crystallization of water to ice for sweet water is of the order of −39° C. (Clausse D (1985): "Research techniques utilizing emulsions", Encyclopedia of emulsion technology, Becher P, Ed, Dekker, New York, Vol 2, p 77). The experimental conditions, defined in terms of pressure, temperature, isotherm duration and gas composition, could then be selected so as to crystallize the aqueous phase in the form of hydrates without ice formation. Further, when preparing the emulsion, an emulsification additive could be added to stabilize the emulsion.

b) Emulsion Sample

A sample of emulsion is removed which is introduced into the calorimeter measuring cell. The quantity of the sample to be introduced depends on the volume of the cell. It is also adjusted as a function of the quantity of water present in the emulsion, the caloric power recorded by the calorimeter being proportional to the quantity of water in the sample.

c) Reference sample

An equal quantity by weight of an inert body is introduced into the reference cell (silicon oil or grease).

d) Pressurization

The two cells are equilibrated at a gas pressure P. The gas phase may be composed of a pure gas or a mixture of different gases. During the subsequent steps, the pressure P in the measuring and reference cells may be kept constant using a pressure regulation system. It is also possible to allow the pressure P to vary during the cooling, reheating, hydrate formation and hydrate dissociation phases.

e) Cooling

Figure 1:
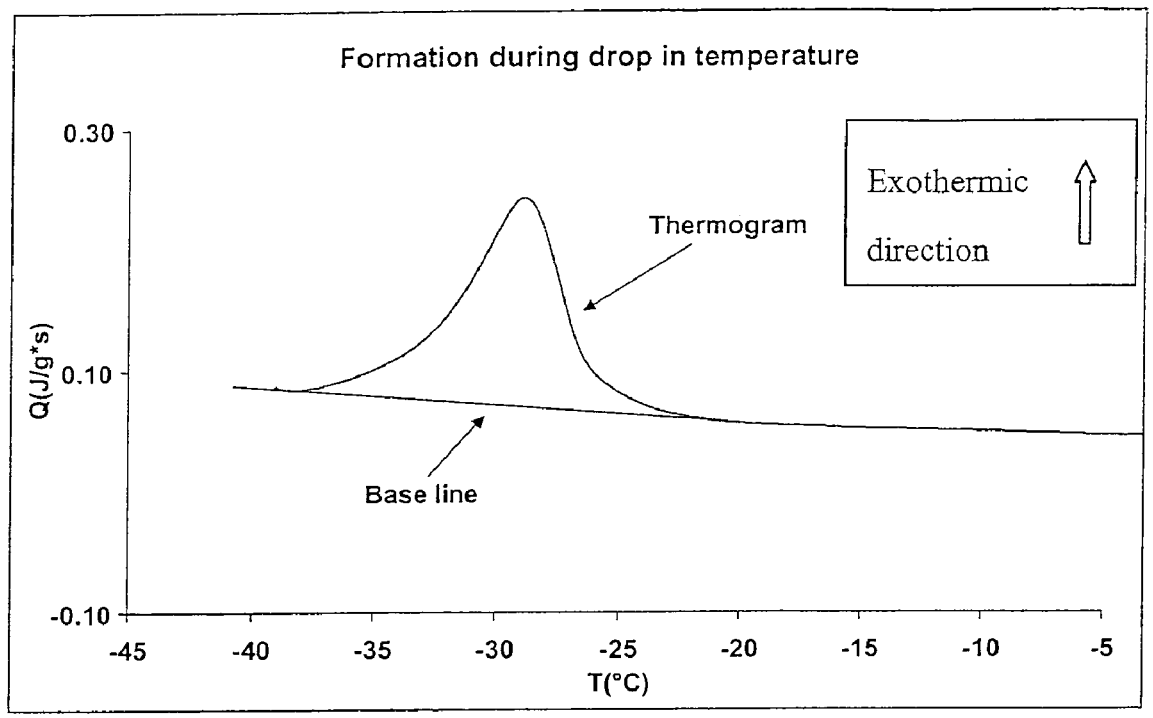
FIG. 1 shows a thermogram corresponding to the formation of hydrates when the temperature is falling. In this case, the power (per unit mass of sample) recorded by the calorimeter is expressed as a function of temperature: Q(T).
Figure 2:
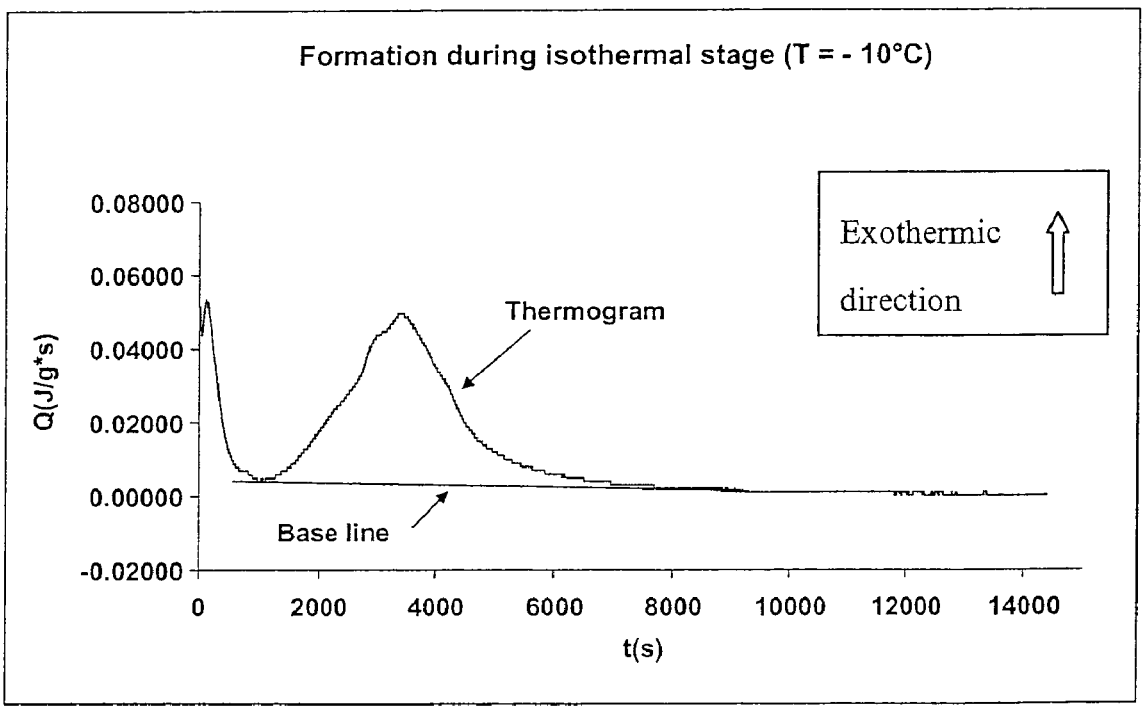
FIG. 2 shows a thermogram corresponding to the formation of hydrates when the temperature is constant at T=−10°

Starting from a temperature $T_1$ which is higher than the melting point of the hydrate $T_0$, the temperature in the measuring and reference cells is reduced to a set temperature $T_2$. The value of $T_0$ may be estimated from the dissociation thermograms shown in FIG. 3 and described by Dalmazzone C, Herzhaft B, Rousseau L, Le Parlouer P, Dalmazzone D (2003): "Prediction of gas hydrates formation with the DSC technique", Proceedings SPE ATCE 2003, Denver (Colo.), 5-8 October 2003, SPE Paper n° 84315). Depending on the choice of set temperature $T_2$, two cases are possible: either hydrates formation takes place as the temperature falls (case shown in FIG. 1), or hydrates formation takes place during the isotherm $T=T_2$ (case shown in FIG. 2). In both cases, the formation peak must return to the base line to ensure that the maximum possible quantity of hydrates has been formed. In particular, in the case of formation over an isotherm $T=T_2$, the temperature $T_2$ must be maintained for a time which is sufficiently long.

f) Reheating

Reheating is carried out to a temperature $T_3$ which is higher than the hydrate melting point $T_0$ (FIG. 3). The temperature $T_3$ must be selected so that the dissociation peak returns to the base line, thus indicating that all of the hydrates formed during the cooling phase have been fully dissociated during the sample reheating phase.

g) Recording the Thermogram

The thermogram Q(T) is traced to identify the dissociation peak. The area under this peak is measured, producing a value which is directly proportional to the quantity of hydrates formed during the cooling phase.

h) Successive Cycles

The formation-dissociation cycle described above is then repeated at least once. The subsequent cycle(s) must be carried out under the same conditions (pressure, temperature, cooling and reheating rates) as in the first cycle.

During the first cycle, the total quantity of hydrates formed is expected to depend on the specific surface area of the water/oil interface. The total quantity of hydrates formed thus depends on the size of the water droplets dispersed in the liquid hydrocarbon phase. If agglomeration takes place during hydrate formation, each hydrate particle will be formed from several water droplets. During dissociation, each hydrate particle will give rise to a new droplet with a larger radius than that of the initial droplets. In the case of agglomeration, the first formation-dissociation cycle will thus lead to a reduction in the specific surface area of the water/oil interface. The thermograms obtained for a second cycle or successive cycles will thus show a reduction in the quantity of hydrates formed. This reduction may be quantified by comparing the area of the dissociation peaks for successive formation-dissociation cycles.

The method of the invention can also be applied to determining the efficacy of an anti-agglomeration additive. To this end, the additive to be determined is introduced at a given concentration (for example 1 to 10 g/liter) into an emulsified water-in-oil system or into one of the two phases, water or oil, before forming said emulsified system and the system undergoes the procedure described above.

The following examples illustrate the invention without limiting its scope.

EXAMPLES

In the examples, the method described above was applied to three oils deriving from offshore fields:

the first oil, designated H1, was an asphaltenic oil that has been used in many studies on the formation and transport of hydrates (Palermo T, Camargo R, Maurel P, Peytavy J L, "Shutdown/restart pilot loop tests with an asphaltenic crude under hydrate formation conditions", in Multiphase 03, 11$^{th}$ International Conference on Multiphase 03, 219-237, Camargo R, Palermo T, "Rheological properties of hydrate suspensions in an asphaltenic crude oil", Proceedings of the 4$^{th}$ International conference on gas hydrates, May 19-23, 2002, Yokohama Symposia, Yokohama, Japan). In particular, it has been shown that this oil has excellent hydrate anti-agglomeration properties;

the second oil, designated H2, was a low asphaltenic oil. It allows very stable water-in-oil emulsions to be formed and prevents hydrate plugging up to moderate water contents (of the order of 30%). In contrast, it does not completely prevent agglomeration phenomena;

the third oil, designated H3, is a low asphaltenic oil containing acidic compounds. It can form very stable water-in-oil emulsions and prevent plugging by hydrates up to moderate water contents (Maurel P, Palermo T, Hurtevent C, Peytavy J L: "Shutdown/restart tests with an acidic crude under hydrate formation conditions for a deepwater development", Proceedings of the 13$^{th}$ International Oil Field Chemistry Symposium, 17-20 March 2002, Geilo, Norway). In contrast, it does not completely prevent agglomeration phenomena.

These three oils were tested in a high pressure (HP) micro DSC VII calorimeter sold by SETARAM under the following conditions:

emulsions prepared using an ULTRA-TURRAX mixer, composed of 30% by weight of sweet water with a pH of 6.5;

quantity of sample (emulsion) in the calorimeter cell: between 10 and 30 mg;

reference sample: silicone oil;

gas phase composition: methane;

pressure in the measuring and reference cells: about 135 bars (unregulated);

temperature ramp: 1° C./min;

temperatures: $T_1=T_3=25°$ C.; $T_2=-10°$ C. (under test conditions: $T_0$ about 15° C.).

The results are shown in FIGS. 4, 5 and 6. These figures show the thermograms recorded during the dissociation phase for two successive cycles. It can clearly be seen that for oil H1 (FIG. 4), the peaks of the two successive cycles are almost superimposed, while for oils H2 (FIG. 5) and H3 (FIG. 6), they are very different. In particular, the peak area associated with the second peak is significantly smaller.

Agglomeration may be quantified by comparing the peak areas for two successive cycles:

| Oil | 1$^{st}$ cycle | 2$^{nd}$ cycle | 1$^{st}$/2$^{nd}$ |
|-----|---------|---------|---------|
| H1  | 141.2   | 141.2   | 1.00    |
| H2  | 143.2   | 57.8    | 2.48    |
| H3  | 138.3   | 30.9    | 4.47    |

Oil H1 does not give rise to agglomeration phenomena between hydrate particles. In contrast, oils H2 and H3 produce agglomeration phenomena.

Agglomeration increases through the class of oils as follows: H1<H2<H3.

The invention claimed is:

1. A method for determining the gas hydrate anti-agglomeration power in an emulsified water-in-oil system in the presence of a gas, comprising:

conducting at least two successive cycles of hydrate formation and dissociation by cooling and reheating a sample of said emulsified water-in-oil system placed in the cell of a calorimeter wherein (A) during hydrate/dissociation, a thermogram is recorded on which a peak of a curve or any other dimension linked to the peak area under the peak is identified, the peak area being characteristic of the quantity of hydrates formed;

(B) during dissociation of the hydrates in a successive cycle or cycles, identifying in the thermograms a peak, the peak area under said peak or any other dimension linked to the peak area is characteristic of the quantity of hydrates formed; and from the change in peak areas under successive (A) and (B) peaks, determining the gas hydrate anti-agglomeration power of the sample, a reduction in said peak area or said other dimension linked to the peak area revealing a weak anti-agglomeration power and conservation of said peak area or said other dimension linked to the peak area revealing a strong anti-agglomeration power.

2. A method according to claim 1, characterized in that it comprises the following steps:
   a) providing or preparing a test emulsified water-in-oil system;
   b) placing a sample of said emulsified water-in-oil system in a measuring cell of a calorimeter comprising said measuring cell and a reference cell;
   c) placing an equal quantity by weight of an inert body in the reference cell of said calorimeter;
   d) bringing the sample and the inert body to a gas pressure P;
   e) starting from a temperature $T_1$ which is higher than the melting point $T_0$ of the hydrate, reducing the temperature in the measuring and reference cells to a set temperature $T_2$ which is maintained for a time sufficient to form at least the major portion of hydrates capable of being formed from the sample located in the measuring cell;
   f) reheating the measuring and reference cells to a temperature $T_3$ which is higher than the melting point $T_0$ of the hydrate to dissociate the hydrates formed in step (e);
   g) during dissociation of the hydrates recording a thermogram on which a peak is identified the area of which, is characteristic of the quantity of hydrates formed;
   h) repeating the cycle of steps (e) to (g) with the resultant sample at least once;
   i) during dissociation of the hydrates in a successive cycle or cycles, identifying in the thermograms a peak the area of which or any other dimension linked to the area is characteristic of the quantity of hydrates formed; and
   j) from the change in areas of the successive peaks, determining the gas hydrate anti-agglomeration power of the sample, a reduction in said area or other dimension revealing a weak anti-agglomeration power and conservation of said area or other dimension revealing a strong anti-agglomeration power.

3. A method according to claim 1, wherein the oil and/or water contain(s) at least one additive selected from corrosion inhibitors, anti-deposition additives comprising minerals, paraffins or asphaltenes, anti-foaming additives, emulsification additives, de-emulsification additives, and anti-hydrate additives comprising thermodynamic inhibitors or kinetic inhibitors.

4. A method according to claim 1, comprising preparing said emulsified water-in-oil system.

5. A method according to claim 4, wherein said prepared emulsified water-in-oil system water droplets with a radius of 1 to 10 µm.

6. A method according to claim 4, wherein during preparation of said emulsified water-in-oil system, an emulsifying additive is added to stabilize the emulsion.

7. A method according to claim 1, wherein said method is conducted under conditions, defined in terms of pressure, temperature, isotherm duration and gas composition, so that the aqueous phase in the water-in-oil emulsion crystallizes in the form of hydrates without the formation of ice.

8. A method according to claim 2, wherein the inert body placed in the reference cell is a silicone oil or grease.

9. A method according to claim 1, wherein an anti-agglomeration additive, is introduced, at a given concentration, into an emulsified water-in-oil system or into one of the two phases, oil or water, prior to forming said emulsified system, and the efficacy of the anti-agglomeration additive is determined.

* * * * *